United States Patent
Haraya et al.

(10) Patent No.: US 9,782,336 B2
(45) Date of Patent: Oct. 10, 2017

(54) MOISTURIZER AND COSMETIC CONTAINING SAME

(71) Applicant: AJINOMOTO CO., INC., Tokyo (JP)

(72) Inventors: Nana Haraya, Kawasaki (JP); Eiko Oshimura, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/455,528

(22) Filed: Mar. 10, 2017

(65) Prior Publication Data

US 2017/0181947 A1 Jun. 29, 2017

Related U.S. Application Data

(63) Continuation of application No. PCT/JP2015/075691, filed on Sep. 10, 2015.

(30) Foreign Application Priority Data

Sep. 10, 2014 (JP) .................. 2014-184373

(51) Int. Cl.
| | |
|---|---|
| A61K 31/40 | (2006.01) |
| A61K 31/19 | (2006.01) |
| A61K 8/49 | (2006.01) |
| A61Q 19/00 | (2006.01) |
| A61K 8/365 | (2006.01) |

(52) U.S. Cl.
CPC ............ *A61K 8/4913* (2013.01); *A61K 8/365* (2013.01); *A61Q 19/00* (2013.01)

(58) Field of Classification Search
CPC ................................ A61K 31/40; A61K 31/19
USPC ................................... 514/423, 557
See application file for complete search history.

(56) References Cited

U.S. PATENT DOCUMENTS

| | | |
|---|---|---|
| 4,837,026 A | 6/1989 | Rajakhyaksha |
| 2002/0127193 A1 | 9/2002 | Ascione et al. |
| 2015/0010489 A1 | 1/2015 | Sugimoto |
| 2015/0038563 A1 | 2/2015 | Fournier |
| 2015/0111859 A1 | 4/2015 | Sugimoto et al. |

FOREIGN PATENT DOCUMENTS

| | | |
|---|---|---|
| FR | 2 900 047 A1 | 10/2007 |
| JP | 9-87126 A | 3/1997 |
| JP | 10-500707 A | 1/1998 |
| JP | 2004-075585 A | 3/2004 |
| JP | 2005-289873 A | 10/2005 |
| JP | 5423002 B2 | 2/2014 |
| WO | WO 87/01935 A1 | 4/1987 |
| WO | WO 2007/148831 A1 | 12/2007 |
| WO | WO 2013/147328 A1 | 10/2013 |
| WO | WO 2013/153330 A2 | 10/2013 |
| WO | WO 2014/007290 A1 | 1/2014 |

OTHER PUBLICATIONS

International Search Report dated Dec. 1, 2015 in PCT/JP2015/075691.

*Primary Examiner* — Raymond Henley, III
(74) *Attorney, Agent, or Firm* — Oblon, McClelland, Maier & Neustadt, L.L.P.

(57) ABSTRACT

The present invention provides a composition containing (A) and (B), which shows a decreased peculiar odor of acylproline and a salt thereof, has a moist feeling and is superior in the stability:

(A) acylproline represented by the formula (1) or a salt thereof

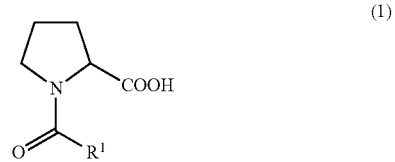

(1)

(wherein an acyl group represented by $R^1$—CO— is an acyl group induced from saturated or unsaturated fatty acid having 3-23 carbon atoms)

(B) a zinc salt of pyrrolidone carboxylate.

20 Claims, No Drawings

MOISTURIZER AND COSMETIC CONTAINING SAME

CROSS REFERENCES TO RELATED APPLICATIONS

This application is a continuation of International Patent Application No. PCT/JP2015/075691, filed on Sep. 10, 2015, and claims priority to Japanese Patent Application No. 2014-184373, filed on Sep. 10, 2014, both of which are incorporated herein by reference in their entireties.

BACKGROUND OF THE INVENTION

Field of the Invention

The present invention relates to a composition comprising particular acylproline or a salt thereof and a zinc salt of pyrrolidone carboxylate and having a suppressed peculiar odor. The present invention relates to the composition further comprising hydroxycarboxylic acid, which is preferable for addition to cosmetics and the like having superior appearance.

Discussion of the Background

Acylamino acid salts are known as low irritative surfactants having high safety, and are particularly used for cleansing agents for sensitive skin. Among them, acyl proline salt is known to be a material useful as a moisturizer having hygroscopicity and moisture retention property (patent documents 1 and 2).

On the other hand, acylamino acid salts such as acylproline salt and the like have defects in that a peculiar odor is produced when the blending amount thereof is increased or when a long time has passed after blending.

For example, as a method for solving the problem of the unpleasant unique odor of base that the acylamino acid salt has, a method of masking odor by using a synthetic flavor has been found. However, some of the people having sensitive skin are allergic to synthetic flavors and such flavors are suggested to pose problems in terms of safety (patent document 3). That is, when an acylamino acid salt is blended in a cosmetic and the like, masking of the peculiar odor is performed. In this case, masking means "adding an aroma", by which deodorizing is not achieved. In addition, since the odor is fixed to cosmetics and so on, application of masking to the manufacture of cosmetics having own scent is avoided.

In addition, a zinc salt of pyrrolidone carboxylate (PCA) (hereinafter sometimes to be abbreviated as Zinc PCA) known to have a sebum suppressive effect, an antibacterial action, a skin astringent effect, an antiaging effect and the like is a useful cosmetic material conventionally used widely for skin external preparations and hair cosmetics for various applications.

DOCUMENT LIST

Patent Documents patent document 1: WO 2013147328
patent document 2: WO 2014007290
patent document 3: JP-A-2004-075585

SUMMARY OF THE INVENTION

Problems to be Solved by the Invention

An object of the present invention is to provide a composition having less odor peculiar to acylproline or a salt thereof, having a moist feeling and superior in the stability.

Means of Solving the Problems

The present inventors have conducted intensive studies in an attempt to solve the above-mentioned problems and found for the first time that the peculiar odor of acylproline or a salt thereof can be reduced by combining acylproline or a salt thereof with Zinc PCA. Even though Zinc PCA is water-soluble, an insoluble precipitate is formed when combined with acyl proline or a salt thereof and its use is restricted. Therefore, they have further studied and found that a transparent solution (composition) having superior stability can be obtained by adding hydroxycarboxylic acid, which resulted in the completion of the present invention.

Accordingly, the present invention provides the following.

[1] A composition comprising the following (A) and (B):
(A) acylproline represented by the formula (1) or a salt thereof

(1)

(wherein an acyl group represented by $R^1$—CO— is an acyl group induced from saturated or unsaturated fatty acid having 3-23 carbon atoms)
(B) a zinc salt of pyrrolidone carboxylate.
[2] The composition of [1], wherein, in (A), the acyl group represented by $R^1$—CO— is an acyl group induced from saturated or unsaturated fatty acid having 6-14 carbon atoms.
[3] The composition of [1] or [2], wherein the acylproline represented by the formula (1) is decanoylproline.
[4] The composition of any one of [1]-[3], wherein the salt of acylproline represented by the formula (1) is a sodium salt.
[5] The composition of any one of [1]-[4], wherein a content of (A) is 0.001 wt %-40 wt % relative to the whole weight of the composition.
[6] The composition of any one of [1]-[5], wherein a content of (B) is 0.01 wt %-10 wt % relative to the whole weight of the composition.
[7] The composition of any one of [1]-[6], further comprising (C) hydroxycarboxylic acid.
[8] The composition of [7], wherein (C) is citric acid.

[9] The composition of [7] or [8], wherein a weight ratio of (B) to (C) [(B)/(C)] is less than 1.
[10] The composition of any one of [1]-[9], which is a moisturizer.
[11] A cosmetic comprising the composition of any one of [1]-[9]
[12] A method of decreasing an odor of the following (A) in a composition comprising (A), comprising a step of placing (B) in coexistence:
(A) acylproline represented by the formula (1) or a salt thereof

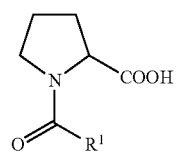

(1)

(wherein an acyl group represented by $R^1$—CO— is an acyl group induced from saturated or unsaturated fatty acid having 3-23 carbon atoms),
(B) a zinc salt of pyrrolidone carboxylate.
[13] A method of suppressing production of an insoluble solid in a composition comprising the following (A) and (B), which comprises a step of placing (C) in coexistence:
(A) acylproline represented by the formula (1) or a salt thereof

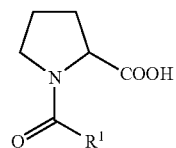

(1)

(wherein an acyl group represented by is an acyl group induced from saturated or unsaturated fatty acid having 3-23 carbon atoms),
(B) a zinc salt of pyrrolidone carboxylate,
(C) hydroxycarboxylic acid.
[14] A method of moisturizing skin, comprising applying, to the skin, a composition comprising the following (A) and (B) in an amount effective for moisturizing the skin:
(A) acylproline represented by the formula (1) or a salt thereof

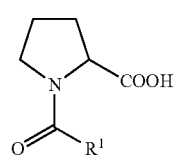

(1)

(wherein an acyl group represented by $R^1$—CO— is an acyl group induced from saturated or unsaturated fatty acid having 3-23 carbon atoms),
(B) a zinc salt of pyrrolidone carboxylate.

Effect of the Invention

According to the present invention, a composition useful as a moisturizer and the like, which has a less peculiar odor derived from acylproline or a salt thereof can be provided.

According to the present invention, moreover, since a transparent state can be maintained even when acylproline or a salt thereof and Zinc PCA are blended, cosmetics and the like having superior appearance can be produced.

In addition, since appearance can be freely changed by coloration and the like, the composition is useful for the production of cosmetics and the like.

DETAILED DESCRIPTION OF THE PREFERRED EMBODIMENTS

The present invention relates to a composition comprising the following (A) and (B), or (A), (B) and (C):
(A) acylproline represented by the formula (1) or a salt thereof

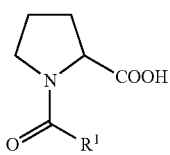

(1)

(wherein an acyl group represented by $R^1$—CO— is an acyl group induced from saturated or unsaturated fatty acid having 3-23 carbon atoms) (hereinafter sometimes to be abbreviated as acylproline of the present invention,
(B) a zinc salt of pyrrolidone carboxylate,
(C) hydroxycarboxylic acid (hereinafter sometimes to be abbreviated as the composition of the present invention).
(A) Acylproline Acylproline to be used in the present invention is represented by the formula (1):

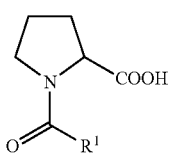

(1)

In the formula (1)

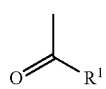

is also shown by $R^1$—CO— in the present specification.

An acyl group represented by $R^1$—CO— is an acyl group induced from fatty acid having 3-23 carbon atoms, preferably an acyl group induced from fatty acid having 4-18 carbon atoms, more preferably an acyl group induced from fatty acid having 6-14 carbon atoms, further preferably an acyl group induced from fatty acid having 10-12 carbon atoms, and a decanoyl group is more preferable. The fatty acid may be saturated or unsaturated, and an acyl group induced from a saturated fatty acid is preferable.

Examples of the acyl group represented by $R^1$—CO— include propanoyl group, isopropanoyl group, butanoyl group, isobutanoyl group, sec-butanoyl group, tert-butanoyl group, pentanoyl group, isopentanoyl group, sec-pentanoyl group, tert-pentanoyl group, hexanoyl group, heptanoyl group, octanoyl group, tert-octanoyl group, 2-ethylhexanoyl group, nonanoyl group, isononanoyl group, decanoyl group, isodecanoyl group, undecanoyl group, lauroyl group, myristoyl group, palmitoyl group, stearoyl group, eicosanoyl group, behenoyl group, undecylenoyl group and oleoyl group and the like. Of these, decanoyl group, lauroyl group, butanoyl group, pentanoyl group, hexanoyl group, octanoyl group, undecanoyl group, myristoyl group, palmitoyl group, stearoyl group, eicosanoyl group, behenoyl group is preferable, decanoyl group, lauroyl group, octanoyl group, hexanoyl group are more preferable, and decanoyl group is further preferable.

To be specific, acylproline represented by the formula (1) is preferably decanoylproline, lauroylproline, butanoylproline, pentanoylproline, hexanoylproline, octanoylproline, undecanoylproline, myristoylproline, palmitoylproline, stearoylproline, eicosanoylproline or behenoylproline is preferable, decanoylproline, lauroylproline, octanoylproline or hexanoylproline is more preferable, and decanoylproline is further preferable.

The long chain acyl group represented by $R^1$—CO— may be an acyl group induced from an acid having a single composition, or an acyl group induced from naturally obtained mixed fatty acids such as coconut oil fatty acid, castor oil fatty acid, olive oil fatty acid, palm oil fatty acid and the like or fatty acid (including branched fatty acid) obtained by synthesis. One kind of these may be used, or two or more kinds selected from the above-mentioned groups may be used in a mixture.

As a salt of the compound of the formula (1), alkali metal salts such as lithium salt, sodium salt, potassium salt and the like; alkaline earth metal salts such as calcium salt, magnesium salt and the like; alkanolamine salts such as triethanolamine salt and the like; ammonium salt; and basic organic salt and the like can be mentioned. Of these, alkali metal salt and ammonium salt are preferable, sodium salt, potassium salt, ammonium salt are more preferable, sodium salt and potassium salt are further preferable, and sodium salt is particularly preferable, from the aspect of solubility.

The production method of the compound represented by the formula (I) of the present invention is not particularly limited, and the compound can be produced easily by combining known methods. To be specific, it can be prepared by the Schotten-Baumann method using proline and acid chloride. In this case, for example, acid chloride and a base such as sodium hydroxide and the like are simultaneously added dropwise. Proline may be an L form or D form, or a mixture thereof. Preferred is an L form.

As the compound represented by the formula (I) or a salt thereof, any of one obtained by the above-mentioned chemical synthesis method, natural one derived from an animal or plant, one obtained by a fermentation method or gene recombination method, and a commercially available product may be used.

The content of acylproline or a salt thereof in the composition of the present invention is preferably 0.001 wt %-40 wt % relative to the whole weight of the composition. The lower limit is more preferably 0.01 wt %, more preferably 0.05 wt %, particularly preferably 0.1 wt %. From the aspect of the texture of the composition, the upper limit is preferably 35 wt %, more preferably 30 wt %, further preferably 20 wt %, still more preferably 15 wt %, particularly preferably 10 wt %, most preferably 5 wt %. The content of the salt of acylproline can be converted from a free form of the above-mentioned acylproline.

(B) Zinc Salt of Pyrrolidone Carboxylate

As the zinc salt of pyrrolidone carboxylate (Zinc PCA) to be used in the present invention, Zinc L-PCA salt or Zinc DL-PCA salt can be used, and Zinc L-PCA salt is preferably used. It is possible to use each of these alone or in a mixture. When a DL form is used, the ratio of the D form and the L fault is not particularly limited. As Zinc PCA, any of one obtained by the above-mentioned chemical synthesis method, natural one derived from an animal or plant, one obtained by a fermentation method or gene recombination method, and a commercially available product may be used.

In the composition of the present invention, the content of (B) Zinc PCA is generally 0.01 wt %-10 wt %. While the lower limit is not particularly limited, 0.1 wt % is preferable, and the upper limit is preferably 5 wt %, more preferably 4 wt %. When the amount added is less than 0.01 wt %, the effect of suppressing the odor of (A), and an anti-inflammatory effect are not sufficiently exhibited, and when an amount exceeding 10 wt % is used, the feeling of use is impaired since a frictional feeling of the skin is produced, both of which are not preferable.

Reduction of odor means that a peculiar odor becomes weak and does not bother, or is not sensed.

Acylproline or a salt thereof of the present invention has both hygroscopicity and moisture retention property.

On the other hand, PCA is one of the components constituting the natural moisturizing factor which is an important component having a role of keeping a moisture component in the stratum corneum. Zinc PCA, which has been functionalized by combining PCA and zinc, is known to have an action to suppress sebum, prevent growth of bacteria, or suppress skin inflammation, by the moisturizing property of PCA and the antibacterial activity of zinc, and is expected to condition the skin to prevent collagen degradation.

Therefore, acylproline or a salt thereof and Zinc PCA can be combined with the above-mentioned (C), and further, other components and used as a moisturizer (composition for moisturization) or an anti-inflammatory agent (composition for anti-inflammation). The composition of the present invention can be blended with cosmetics (including quasi-drugs) and the like.

In the present invention, moisturizer means one that gives moist texture and moist feeling to the skin and hair.

In the present invention, an anti-inflammatory agent means a useful preparation that suppresses skin inflammation.

For example, in the composition of the present invention, (A) is 1 part by weight and (B) is generally 0.1-20 parts by weight, preferably 0.2-10 parts by weight, more preferably 0.2-4.0 parts by weight. When they are within the aforementioned ranges, a composition superior in the effect of reducing the peculiar odor of (A) and in a moisturizing effect can be provided.

(C) Hydroxycarboxylic Acid

The hydroxycarboxylic acid to be used in the present invention is a carboxylic acid having a hydroxy group as well, and is widely distributed in the body in, for example, TCA circuit and the like. As hydroxycarboxylic acid, any of one obtained by a chemical synthesis method, natural one derived from an animal or plant, one obtained by a fermentation method or gene recombination method, and a commercially available product may be used.

As the hydroxycarboxylic acid, aliphatic hydroxy acid: glycolic acid, lactic acid, tartronic acid, glycolic acid, hydroxybutyric acid (2-hydroxybutyric acid, 3-hydroxybutyric acid, γ-hydroxybutyric acid), malic acid, tartaric acid, citramalic acid, citric acid, isocitric acid, leucine acid, mevalonic acid, pantoic acid, pantothenic acid, ricinoleic acid, ricinelaidic acid, cerebronic acid, quinic acid, shikimic acid and the like; aromatic hydroxy acid: monohydroxybenzoic acid derivative (salicylic acid, creosotic acid (homosalicyl acid, hydroxy(methyl)benzoic acid), vanillin acid, syringic acid etc.) and the like; dihydroxybenzoic acid derivative (pyrocatechuic acid, resorcylic acid, protocatechuic acid, gentisic acid, orsellinic acid etc.); trihydroxybenzoic acid derivative (gallic acid etc.); phenylacetic acid derivative (mandelic acid, benzyl acid, atrolactic acid etc.); cinnamic acid, hydroxycinnamic acid derivative (melilotic acid, phloretic acid, coumaric acid, umbellic acid, caffeic acid, ferulic acid, sinapic acid) and the like can be mentioned. Of these, from the aspect of broad utility, specifically, glycolic acid, lactic acid, hydroxybutyric acid, malic acid, tartaric acid, citramalic acid, citric acid, isocitric acid, leucine acid, mevalonic acid, pantoic acid, pantothenic acid, ricinoleic acid, cerebronic acid, shikimic acid, salicylic acid, hydroxy(methyl)benzoic acid, protocatechuic acid, orsellinic acid, gallic acid, mandelic acid, benzyl acid, cinnamic acid, ferulic acid are preferable, glycolic acid, lactic acid, hydroxybutyric acid, malic acid, tartaric acid, citric acid, pantoic acid, pantothenic acid, shikimic acid, salicylic acid, hydroxy(methyl)benzoic acid, protocatechuic acid, gallic acid, mandelic acid, cinnamic acid, ferulic acid are more preferable, and citric acid is particularly preferable.

In the composition of the present invention, the content of the hydroxycarboxylic acid is generally 0.01 wt %-10 wt %, preferably 0.05 wt %-5 wt %. When they are within the aforementioned ranges, a composition containing (A) and (B) which is a transparent solution free of precipitation can be provided. When the amount exceeds 10 wt %, stimulation may be felt.

Particularly, from the aspect of solubility of the precipitates produced in the composition containing (A) and (B), a weight ratio of (B) to (C) [(B)/(C)] is generally less than 1, preferably not more than 0.98, more preferably not more than 0.90. When they are within these ranges of the numerical values, a transparent solution can be provided without producing precipitates. While the lower limit is not particularly set, it is not less than 0.01, preferably not less than 0.05.

The production method of the composition of the present invention is not particularly limited except that the (B)/(C) ratio is adjusted when (C) is added, and the below-mentioned additives are added as appropriate, wherein known steps may be combined appropriately.

Cosmetics containing the composition of the present invention are also encompassed in the present invention. Examples of the cosmetics (cosmetic) include skin cosmetics such as facial cleanser, skin lotion, milky lotion, cream, gel, serum, mask, soap, body shampoo, face powder, foundation, lip rouge, blush, eyeliner, mascara, eye shadow, eyebrow pencil and the like, and hair cosmetics such as shampoo, rinse, conditioner, hair styling agent, hair treatment and the like. While any cosmetics can be provided, skin cosmetics requiring moisturizing and hair cosmetics are preferable, and specifically, facial cleanser, skin lotion, milky lotion, cream, gel, serum, body shampoo and shampoo are more preferable.

Cosmetics may contain components that may be generally added to cosmetics as long as the effects of the present invention are not inhibited. Specifically, oil solution, chelating agent, surfactant, powder (organic and inorganic powders), amino acids, polyamino acid and a salt thereof, sugar alcohol and alkylene oxide adduct thereof, lower alcohol, animal and plant extracts, nucleic acid, vitamin, enzyme, anti-inflammatory agent, antimicrobial agent, preservative, antioxidant, moisturizer, thickener, viscosity modifier, ultraviolet absorber, adiaphoretic, pigment, dye, oxidation dye, pH adjuster, pearly sheen agent, wetting agent and the like can be mentioned. These are mere examples, and components other than these may be contained.

Examples of the oil solution include fatty acids such as isostearic acid, undecylenoic acid, oleic acid and the like; esters such as myristyl myristate, hexyl laurate, decyl oleate, isopropyl myristate, hexyldecyl dimethyl octanoate, glycerine monostearate, diethyl phthalate, ethylene glycol monostearate, cetyl octanoate, octyl oxystearate, benzoic acid alkyl ester and the like; hydrocarbons such as liquid paraffin, polyisobutene, petrolatum, squalane and the like; wax such as lanolin, reduced lanolin, carnauba wax and the like; silicone oil; fats and oils such as mink oil, cacao oil, coconut oil, palm kernel oil, camellia oil, sesame oil, castor oil, olive oil, jojoba oil and the like; cooligomers of ethylene and α-olefin, and the like.

A particular example of the silicone oil is silicone oil selected from ether-modified silicone such as methylpolysiloxane, polymeric methylpolysiloxane, polyoxyethylene/methylpolysiloxane copolymer, polyoxypropylene/methylpolysiloxane copolymer and poly(oxyethylene, oxypropylene)/methylpolysiloxane copolymer and the like; cyclic silicone such as stearoxymethylpolysiloxane, stearoxytrimethylsilane, methylhydrogen polysiloxane, decamethylcyclopentasiloxane, octamethylcyclotetrasiloxane, tetrahydrotetramethylcyclotetrasiloxane, methylcyclopolysiloxane, dodecamethylcyclohexasiloxane and the like; amino-modified silicone such as methylphenylpolysiloxane, trimethylsiloxysilicate, aminoethylaminopropylsiloxane/dimethylsiloxane copolymer and the like, silanol-modified polysiloxane, alkoxy-modified polysiloxane, fatty acid-modified polysiloxane, fluorine-modified polysiloxane, epoxy-modified polysiloxane, alkoxy-modified polysiloxane perfluoropolyether, polyvinyl acetate dimethyl polysiloxane, and mixtures thereof.

While the chelating agent is not particularly limited, preferable examples thereof include a chelating agent selected from triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid (EDTA), diethylenetriamine pentaacetic acid, acetylacetone and a salt thereof, and mixtures thereof and the like.

Examples of the surfactant include anionic surfactants such as N-long chain acylamino acid salt (N-long chain acyl acidic amino acid salt, N-long chain acyl neutral amino acid salt and the like), N-long chain fatty acid acyl-N-methyl taurate, alkyl sulfate and an alkylene oxide adduct thereof, fatty acid amide ether sulfate, metal salt and weak base salt of fatty acid, sulfosuccinate surfactant, alkylphosphate and an alkylene oxide adduct thereof, alkyl ether carboxylic acid and the like; non-ionic surfactants such as ether-type surfactant (glycerine ether and an alkylene oxide adduct thereof and the like), ether ester-type surfactant (an alkylene oxide adduct of glycerine ester, an alkylene oxide adduct of sorbitan ester and the like), ester-type surfactant (polyoxyalkylene fatty acid ester, glycerine ester, fatty acid polyglycerine ester, sorbitan ester, sucrose fatty acid ester and the like), alkylglucosides, hydrogenated castor oil pyroglutamic acid diester and an ethylene oxide adduct thereof, nitrogen-containing surfactants (fatty acid alkanolamide and the like); cationic surfactants such as quaternary ammonium salt (alkylammonium chloride, dialkylammonium chloride and the like), aromatic quaternary ammonium salt (benzalkonium salt and the like), fatty acid acyl arginine ester and the like; amphoteric surfactant such as betaine-type surfactant (carboxybetaine and the like), aminocarboxylic acid-type surfactant, imidazoline-type surfactant and the like, and the like.

Examples of the powder include resin powder such as nylon beads, silicone beads and the like, nylon powder, metal fatty acid soap, yellow iron oxide, red iron oxide, black iron oxide, chromium oxide, cobalt oxide, carbon black, ultramarine, iron blue, zinc oxide, titanium oxide, zirconium oxide, silicon oxide, aluminum oxide, cerium oxide, titanated mica, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, fine particles of titanium oxide, fine particles of zinc oxide, fine particles of iron oxide, acyl amino acid such as acyl lysine, acylglutamic acid, acylarginine, acylglycine and the like and the like. Furthermore, surface treatment such as silicone treatment, fluorine compound treatment, silane coupling agent treatment, silane treatment-organic titanate treatment, acylated lysine treatment, fatty acid treatment, metallic soap treatment, oil solution treatment, amino acid treatment and the like may be applied.

Examples of the amino acid include glycine, alanine, serine, threonine, arginine, glutamic acid, aspartic acid, isoleucine, leucine, valine and the like.

Examples of the polyamino acid and a salt thereof include polyglutamic acid, polyaspartic acid and the like.

Examples of the sugar alcohol and alkylene oxide adduct thereof include mannitol, sorbitol and the like.

Examples of the lower alcohol include ethanol, propanol and the like. Examples of other additive include animal and plant extracts such as lecithin, gelatin and the like; nucleic acids such as disodium 5'-inosinate, disodium 5'-uridylate and the like; vitamins such as vitamin A, C etc., a derivative thereof and the like; enzymes such as papain, protease and the like; anti-inflammatory agents such as potassium glycyrrhizate and the like; antimicrobial agents such as triclosan, trichloro calban, octopirox, zinc pyrithione and the like; preservatives such as methylparaben, butylparaben and the like; antioxidants such as dibutylhydroxytoluene and the like; moisturizers such as isopentyldiol, luvitol and the like; thickeners such as hydroxypropyl starch phosphoric acid and the like; viscosity modifiers such as polyoxyalkylene sorbitan ester, polyoxyethylene glycol distearate, ethanol and the like; ultraviolet absorbers such as octyl-methoxycinnamate and the like; adiaphoretics such as aluminum oxide and the like; pigments such as titanium dioxide and the like; dyes such as tar dye, inorganic dye, dye derived from natural-base and the like; fragrances, pH adjusters such as citric acid, trisodium citrate, sodium carbonate, phosphoric acid and the like; pearly sheen agents such as ethylene glycol distearate and the like; humectants such as propylene glycol and the like; and the like.

A moisturizing method or inflammation suppressive method including applying a composition containing (A), (B) and (C) to a subject is also encompassed in the present invention. The definition of each is as described above.

The application here means topically applying acylproline or a salt thereof singly or effective amounts of (A) and (B) in the aforementioned form of a composition or cosmetic, to the skin etc. of a subject in need thereof. For example, it includes application of a form of cream onto the skin, gel and the like or spraying a liquid preparation to the skin and the like. Generally, the "effective amount" varies depending on the age, sex, symptom, application site of the subject, dosage form of composition and the like, and an amount of the aforementioned composition and the like to be applied according to the symptoms can be mentioned.

A method of decreasing the odor of (A), which includes a step of placing (B) in coexistence, is also encompassed in the present invention.

A method of suppressing production of an insoluble solid in the composition containing (A) and (B), which includes a step of placing (C) in coexistence, is also encompassed in the present invention. According to the method of the present invention, a simple coexistence of (C) can suppress production of an insoluble solid, make the composition transparent, and prepare a composition optimal for cosmetics and the like. The definition, amount etc. of each are as described above.

A method of moisturizing skin, comprising applying, to the skin, an effective amount of the above-mentioned composition containing (A) and (B) for moisturizing the skin is also encompassed in the present invention.

In addition, a beauty treatment method for non-therapeutic skin care or skin makeup, which includes applying the above-mentioned composition containing (A) and (B) to the skin is also encompassed in the present invention. The definition etc. of the composition follow those described above.

EXAMPLES

The present invention is explained in more detail in the following by referring to Examples. However, the present invention is not limited by the following Examples.

<Synthetic Example 1> Synthesis of Decanoylproline

Proline (manufactured by Ajinomoto Co., Inc.) (34.54 g) was dissolved in 100 g of water, and decanoyl chloride (manufactured by Tokyo Chemical Industry Co., Ltd.) (52.01 g) and 25% aqueous sodium hydroxide solution were added while adjusting the mixture to pH 12. The mixture was neutralized with 75% sulfuric acid, and the aqueous layer was removed. Furthermore, water and ethyl acetate were added and the aqueous layer was removed. Ethyl acetate was evaporated under reduced pressure to give decanoylproline (68.12 g).

<Synthetic Example 2> Synthesis of Decanoyl Prolinate Sodium Salt

Decanoylproline obtained in Synthetic Example 1 was suspended in a suitable amount of water and neutralized with sodium hydroxide up to pH 7, and concentration-dried to give decanoyl prolinate sodium salt.

<Synthetic Example 3> Synthesis of Lauroylproline

Using proline and lauroyl chloride (manufactured by Tokyo Chemical Industry Co., Ltd.) and in the same manner as in Synthetic Example 1, lauroylproline was obtained.

<Synthetic Example 4> Synthesis of Lauroylproline Sodium Salt

Using lauroylproline obtained in Synthetic Example 3 and in the same manner as in Synthetic Example 2, lauroylproline sodium salt was obtained.

TABLE 1

| | | Preparation Example | | | | | | | | | |
|---|---|---|---|---|---|---|---|---|---|---|---|
| | | 1 | 2 | 3 | 4 | 5 | 6 | 7 | 8 | 9 | 10 |
| Component A | decanoylproline Na | 0.20 | 0.50 | 0.20 | 0.50 | 0.20 | 0.50 | 0.40 | 0.20 | 0 | 0.50 |
| Component B | Zinc PCA | 0.20 | 0.20 | 0.50 | 0.50 | 1.00 | 1.00 | 0.50 | 1.00 | 1.00 | 0 |
| Component C | citric acid | 0.60 | 0.60 | 0.60 | 0.60 | 0.60 | 0.60 | 0.50 | 0 | 0 | 0.60 |
| | water | balance | balance | balance | balance | balance | balance | balance | balance | balance | balance |
| | total | 100 | 100 | 100 | 100 | 100 | 100 | 100 | 100 | 100 | 100 |
| | evaluation 1: clarity and color of solution | ○ | ○ | ○ | ○ | x | x | x | x | ○ | — |
| | evaluation 2: peculiar odor reduction | — | ○ | ○ | — | — | — | — | ○ | — | x |
| | evaluation 3: moist feeling | — | ○ | ○ | — | — | — | — | — | x | ○ |
| | B/C ratio | 0.33 | 0.33 | 0.83 | 0.83 | 1.67 | 1.67 | 1.00 | — | — | — |

Decanoylproline Na, Zinc PCA, and citric acid were added to water at a concentration described in Table 1, and pH was adjusted to 5.7 with hydrochloric acid or aqueous sodium hydroxide solution. The composition for test was completely tightly sealed in a 30 mL glass bottle, stored at 45° C. for 4 months, cooled to room temperature and the following evaluation was performed.

<Formulation Evaluation 1> Clarity and Color of Solution

As mentioned above, clarity and color of the prepared composition were confirmed, and evaluated according to the following criteria.

○ transparent aqueous solution was obtained.

x precipitation was confirmed.

<Formulation Evaluation 2> Peculiar Odor

The peculiar odor of the composition of the present invention was tested by 8 healthy men and women. Whether the peculiar odor of the composition prepared as mentioned above caught his/her attention was searched, and evaluated according to the following criteria.

○ Not less than 6 test subjects denied concern about the peculiar odor.

Δ 4 or 5 test subjects denied concern about the peculiar odor.

x Not more than 3 test subjects denied concern about the peculiar odor.

The test subjects were made to recognize the odor of decanoylproline Na in advance as the peculiar odor of component A.

<Formulation Evaluation 3> Moist Feeling

The moist feeling of the composition of the present invention was tested by 8 healthy men and women. The composition prepared as mentioned above was applied to the inside of a 8×2 cm skin area of the inner surface of the forearm, and whether a moist feeling was sensed was searched, and evaluated according to the following criteria.

○ Not less than 6 test subjects admitted the moist feeling.

Δ 4 or 5 test subjects admitted the moist feeling.

x Not more than 3 subjects admitted the moist feeling.

Each amount in Examples is shown in wt %. In the Table, indication of % is omitted, and used only the numerical value showing the amount. In the Table, "–" shows that evaluation was not performed.

As is clear from Table 1, the combined use of Zinc PCA and decanoylproline Na decreased the peculiar odor and a composition superior in the moist feeling was obtained. It was found that an insoluble solid in the composition is dissolved when the B/C ratio is less than 1.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising:

(A) at least one acylproline represented by formula (1) or a salt thereof

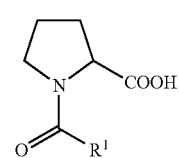

wherein R¹—CO— is an acyl group derived from a saturated or unsaturated fatty acid having 3 to 23 carbon atoms; and
(B) a zinc salt of pyrrolidone carboxylate.

2. The composition according to claim 1, wherein R¹—CO— is an acyl group derived from a saturated or unsaturated fatty acid having 6 to 14 carbon atoms.

3. The composition according to claim 1, wherein (A) said acylproline represented by formula (1) is decanoylproline.

4. The composition according to claim 1, wherein said salt of said acylproline represented by formula (1) is a sodium salt.

5. The composition according to claim 1, wherein (A) said at least one acylproline represented by formula (1) or a salt thereof is present in an amount of 0.001 wt % to 40 wt % relative to the total weight of said composition.

6. The composition according to claim 1, wherein (B) said zinc salt of pyrrolidone carboxylate is present in an amount of 0.01 wt % to 10 wt % relative to the total weight of said composition.

7. The composition according to claim 1, further comprising:
(C) at least one hydroxycarboxylic acid.

8. The composition according to claim 7, wherein (C) said at least one hydroxycarboxylic acid is citric acid.

9. The composition according to claim 7, wherein a weight ratio of (B) to (C) [(B)/(C)] is less than 1.

10. The composition according to claim 1, which is a moisturizer.

11. A cosmetic, comprising a composition according to claim 1.

12. A method of decreasing an odor of a composition comprising:
(A) an acylproline represented by formula (1) or a salt thereof

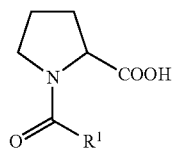

(1)

wherein R¹—CO— is an acyl group derived from a saturated or unsaturated fatty acid having 3 to 23 carbon atoms,
said method comprising combining in said composition:
(B) a zinc salt of pyrrolidone carboxylate.

13. The method according to claim 12, wherein R¹—CO— is an acyl group derived from a saturated or unsaturated fatty acid having 6 to 14 carbon atoms.

14. The method according to claim 12, wherein (A) said acylproline represented by formula (1) is decanoylproline.

15. The method according to claim 12, wherein said salt of said acylproline represented by formula (1) is a sodium salt.

16. A method of suppressing production of an insoluble solid in a composition comprising:
(A) at least one acylproline represented by formula (1) or a salt thereof

(1)

wherein R¹—CO— is an acyl group derived from a saturated or unsaturated fatty acid having 3 to 23 carbon atoms; and
(B) a zinc salt of pyrrolidone carboxylate, said method comprising combining in said composition:
(C) at least one hydroxycarboxylic acid.

17. The method according to claim 16, wherein R¹—CO— is an acyl group derived from a saturated or unsaturated fatty acid having 6 to 14 carbon atoms.

18. The method according to claim 16, wherein (A) said acylproline represented by formula (1) is decanoylproline.

19. The method according to claim 16, wherein said salt of said acylproline represented by formula (1) is a sodium salt.

20. The method according to claim 16, wherein (C) said at least one hydroxycarboxylic acid is citric acid.

* * * * *